United States Patent [19]

Omata et al.

[11] Patent Number: 4,668,226
[45] Date of Patent: May 26, 1987

[54] INJECTION NEEDLE ASSEMBLY FOR ENDOSCOPE

[75] Inventors: Katumi Omata, Sagamihara; Tetsuji Ishida, Tokyo, both of Japan

[73] Assignee: Olympus Optical Co., Ltd., Tokyo, Japan

[21] Appl. No.: 783,219

[22] Filed: Oct. 2, 1985

[30] Foreign Application Priority Data

Oct. 22, 1984 [JP]  Japan ................................ 59-159494

[51] Int. Cl.$^4$ .............................................. A61B 1/00
[52] U.S. Cl. .................................. 604/272; 604/164; 604/198; 604/283; 128/4
[58] Field of Search .................. 604/272, 164–169, 604/198, 51, 283; 128/4

[56] References Cited

U.S. PATENT DOCUMENTS

| | | | |
|---|---|---|---|
| 3,659,610 | 5/1972 | Cimber | 604/157 |
| 3,960,143 | 6/1976 | Terada | 128/4 |
| 4,222,380 | 9/1980 | Terayama | 128/4 |
| 4,249,541 | 2/1981 | Pratt | 604/165 |
| 4,321,915 | 3/1982 | Leighton et al. | 128/4 |
| 4,372,295 | 3/1983 | Heckele | 128/4 |

Primary Examiner—Stephen C. Pellegrino
Assistant Examiner—John D. Ferros

[57] ABSTRACT

An injection needle assembly has an elongate, flexible liquid feed tube adapted to be inserted into the insertion channel of an endoscope. A needle is fixed to the distal end of the tube and adapted to be stuck in the body wall. A rigid connecting pipe is fixed on the outer surface of the proximal end portion of the tube. The connecting pipe is fixedly inserted into a fitting portion of a connector.

8 Claims, 6 Drawing Figures

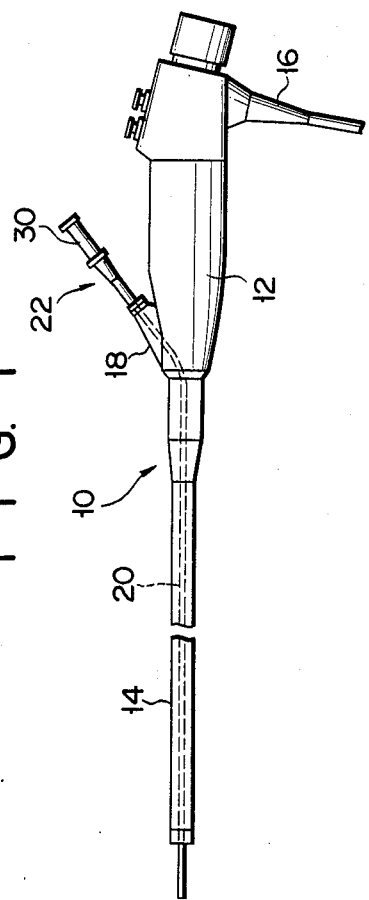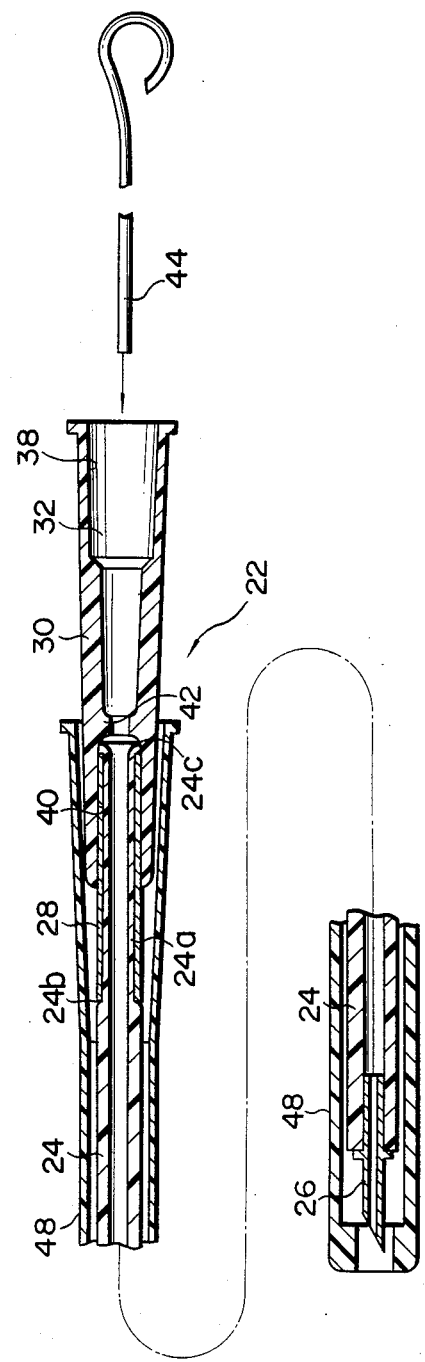

INJECTION NEEDLE ASSEMBLY FOR ENDOSCOPE

BACKGROUND OF THE INVENTION

The present invention relates to an injection needle assembly used in combination with an endoscope.

Injection needle assemblies of this type comprise an elongate liquid feed tube made of resin and adapted to be inserted into an insertion channel of an endoscope. The tube has a needle at its distal end, and a connector at its proximal end. The connector can be coupled to an injector. The connector is a hollow cylinder, and a first metallic pipe is fixedly inserted in that end of the connector which is attached to the tube. One half of the first pipe projects from the connector. A second metallic pipe is fixedly inserted in the first pipe, with one end portion projecting from the first pipe. The projecting portion of the second pipe is fixedly inserted in the proximal end of the liquid feed tube.

To insert the injection needle assembly into the insertion channel of an endoscope, a stylet (wire) is inserted into the liquid feed tube through the connector to enhance the rigidity of the liquid feed tube to be inserted into a flexible sheath and then the needle assembly is inserted into the insertion channel together with the sheath.

As the stylet is inserted into the tube, however, it rubs the inner surface of the second pipe, producing metal dust. The first and second pipes are formed by cutting a very long pipe into pieces of a desired size. These pipes, however, are so narrow that the chips produced during the cutting remain in the pipes. When a medical fluid is injected into the body cavity through the injection needle assembly, it may mix with the metal dust or chips.

The first pipe is fastened to the connector by an adhesive, and the liquid feed tube is also fastened by an adhesive to the second pipe. The adhesive may flow into the pipes and the liquid feed tube. In such a case, the adhesive will hinder the insertion of the stylet. Furthermore, since the inner peripheral surface of the liquid feed tube is chemically treated for higher bonding strength, the dried treatment agent will possibly penetrate the liquid feed tube during the bonding work.

SUMMARY OF THE INVENTION

The present invention is contrived in consideration of these circumstances, and is intended to provide an injection needle assembly capable of preventing penetration of metal dust or chips produced during manufacture or powdered chemicals or production of metal dust during stylet insertion, and permitting reduction in manufacturing cost.

In order to achieve the above object, an injection needle assembly according to the present invention comprises an elongate, flexible liquid feed tube adapted to be inserted into an insertion channel of an endoscope, a needle fixed to the distal end of the liquid feed tube and adapted to be stuck in the body wall, a rigid connecting pipe fixed to the outer peripheral surface of the proximal end portion of the liquid feed tube, and a substantially cylindrical connector having a fitting portion at one end opening thereof in which the connecting pipe is fixedly inserted and a connecting portion at the other end opening adapted to be connected to an injector for feeding a liquid into the liquid feed tube.

BRIEF DESCRIPTION OF THE DRAWINGS

FIGS. 1 to 4 show an injection needle assembly according to a first embodiment of the present invention, in which FIG. 1 is a schematic view showing the injection needle assembly inserted in an insertion channel of an endoscope, FIG. 2 is a longitudinal sectional view of the needle assembly, FIG. 3 is an enlarged sectional view showing the principal part of the needle assembly, and FIG. 4 is a cutaway side view showing the needle assembly connected to an injector;

DETAILED DESCRIPTION OF THE PREFERRED EMBODIMENTS

Figure 3:
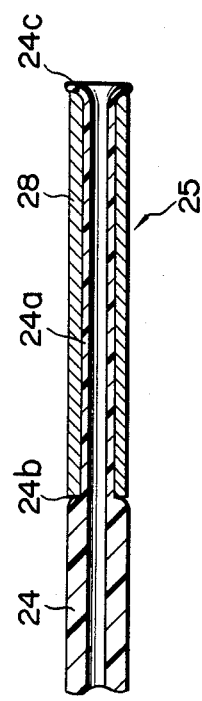

Preferred embodiments of the present invention will now be described in detail with reference to the accompanying drawings.

As shown in FIG. 1, an endoscope 10 generally comprises an operating section 12, a flexible insertion section 14, and an universal cord 16 connected to the operating section 12. The operating section 12 is provided with an insertion mouthpiece 18, from which extends an insertion channel 20 penetrating the operating section 12 and the insertion section 14 and opening to the distal end of the insertion section 14. An injection needle assembly 22 according to the present invention is inserted in the insertion channel 20.

As shown in FIG. 2, the injection needle assembly 22 comprises an elongate liquid feed tube 24 which is adapted to be inserted into the insertion channel 20 of the endoscope 10. The tube 24 is a relatively flexible tube made of resin. A needle 26 to be stuck in the body wall is fixed to the distal end of the liquid feed tube 24, while a connector 30 is fixedly fitted on the other end portion of the tube 24 by means of a rigid connecting pipe 28.

Figure 4:
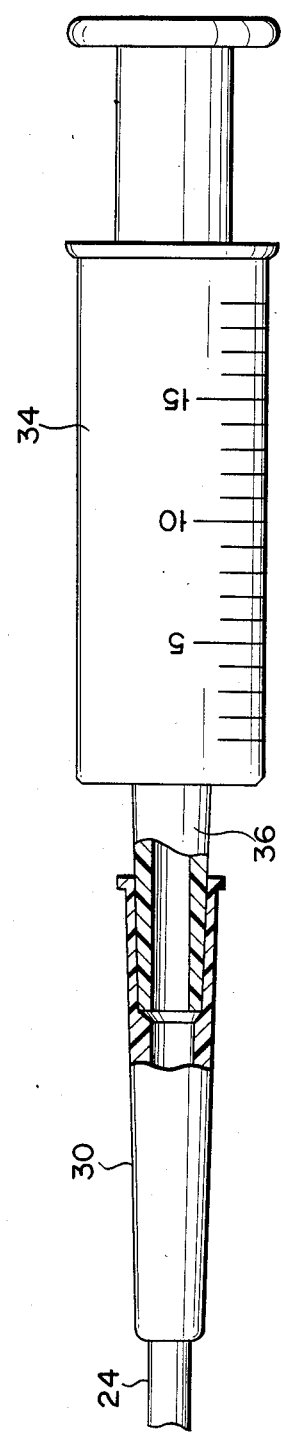

The connector 30 is substantially in the form of a hollow cylinder. One end portion of the bore of the connector 30 constitutes a connecting portion 32, which is adapted to receive a mouthpiece portion 36 of an injector 34, as shown in FIG. 4. An inner peripheral surface 38 of the connecting portion 32 is tapered from one end of the connector 30 toward the other end, corresponding in shape to the mouthpiece portion of the injector 34. The other end portion of the bore of the connector 30 constitutes a fitting hole 40 as a fitting portion to receive the proximal end portion of the liquid feed tube 24. The fitting hole 40 has a diameter substantially equal to the outside diameter of the connecting pipe 28, and a ring-shaped projection 42 is formed on the inner surface of the fitting hole at the inner end thereof.

As shown in FIGS. 2 and 3, a proximal end portion 24a of the liquid feed tube 24 is smaller in outside diameter or in wall thickness than the other portion of the tube 24. The proximal end portion 24a may be formed by, for example, heating the liquid tube 24 and then drawing its one end portion to make it thinner. A ring-shaped shoulder portion 24b is formed on the boundary between the proximal end portion 24a and the other portion of the liquid feed tube 24. The proximal end portion 24a is inserted in the metallic connecting pipe 28 so that the shoulder portion 24b abuts against one end of the connecting pipe 28. The connecting pipe 28 is substantially as long as the proximal end portion 24a. An end edge 24c of the proximal end portion 24a is bent radially outward to engage the other end of the connecting pipe 28, so that the connecting pipe 28 is held on the outer peripheral surface of the proximal end portion by the shoulder portion 24b and the end edge 24c. The shoulder portion 24b and the end edge 24c constitute retaining means 25 of the present invention. The connecting pipe 28, along with the proximal end portion 24a of the liquid feed tube 24, is fitted by force into the fitting hole 40 of the connector 30 until the end edge 24c of the proximal end portion 24a abuts against the projection 42.

There will now be described the way of the injection needle assembly 22 with the above-mentioned construction is used with the endoscope 10.

First, the insertion section 14 of the endoscope 10 is inserted into the body cavity. Then, the rigidity of the liquid feed tube 24 is enhanced by inserting a stylet 44 into the tube 24 through the connector 30. In this state, the liquid feed tube 24 is inserted into a flexible sheath 48. Then, the tube 24, along with the sheath 48, is inserted into the insertion channel 20 through the insertion mouthpiece 18 of the endoscope 10 so that the distal end of the sheath 48 projects from the distal end of the insertion section 14. Thereafter, the liquid feed tube 24 is further pushed in to cause the needle 26 to stick in a desired region of the body wall. The stylet 44 is drawn out of the injection needle assembly 22, and the mouthpiece portion 36 of the injector 34 is then fitted in the connecting portion 32 of the connector 30. As the injector 34 is operated in this state, a desired medical fluid is injected into the body wall through the connector 30, liquid feed tube 24, and needle 26.

Constructed in this manner, the injection needle assembly has the following functions and effects. The proximal end portion of the liquid feed tube is fixed to the connector by means of the rigid connecting pipe fitted on the outer peripheral surface thereof. Therefore, no metal or other rigid portions are exposed to the inner peripheral surface of the liquid feed tube, so that there is no possibility of metal dust or chips being produced in the liquid feed tube while the stylet is being inserted into the liquid feed tube. Even if any metal dust produced during the manufacture of the connecting pipe remains in the pipe, moreover, it will never be allowed to penetrate the liquid feed tube. The connecting pipe is fixed to the outer peripheral surface of the proximal end portion of the liquid feed tube by inserting the proximal end portion into the connecting pipe and bending the end edge of the proximal end portion outwardly. It is therefore unnecessary to use any adhesive agent or auxiliary agent for improved adhesive strength, and it is impossible for such agents to penetrate the liquid feed tube. Thus, the medical fluid will never be misguidedly accompanied by any metal dust or powdered chemicals during its injection into the body wall, ensuring the reliability of the injection needle assembly as a medical instrument. Further, the insertion of the stylet is not very likely to be retarded by an adhesive agent.

Furthermore, the liquid feed tube and the connector are connected by means of the single connecting pipe without the use of a plurality of connecting pipes which should be required by a prior art needle assembly. This may lead to simpler manufacture and lower manufacturing cost.

The present invention is not limited to the embodiment described above, and various changes and modifications may be effected therein by one skilled in the art without departing from the scope of the invention.

Figure 5:
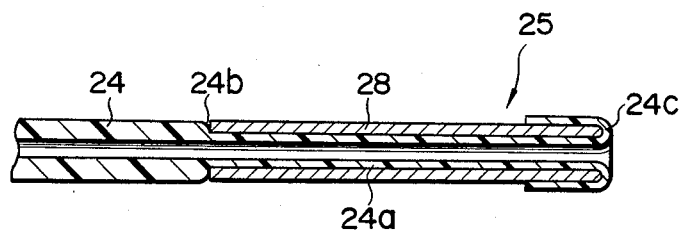
FIG. 5 is an enlarged sectional view showing the principal part of an injection needle assembly according to a second embodiment of the invention.

As shown in FIG. 5, for example, the proximal end portion 24a of the liquid feed tube 24 may be made longer than the connecting pipe 28 so that the connecting pipe is held on the outer peripheral surface of the proximal end portion by folding back the end edge 24c of the proximal end portion onto the outer peripheral surface of the connecting pipe.

Figure 6:
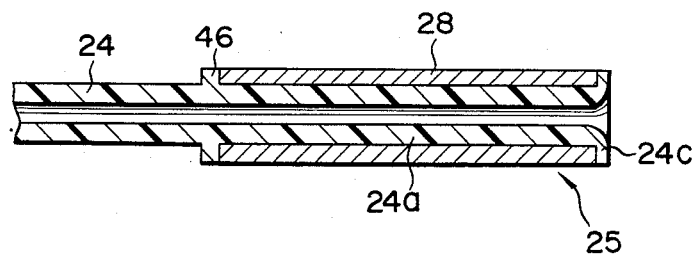
FIG. 6 is a sectional view showing the principal part of an injection needle assembly according to a third embodiment of the invention.

As shown in FIG. 6, moreover, a ring-shaped projection 46 may be formed on the outer peripheral surface of the liquid feed tube 24, instead of reducing the wall thickness of the proximal end portion 24a, so that the projection 46 and the bent end edge 24c of the proximal end portion constitute the retaining means 25 for holding the connecting pipe 28.

The connecting pipe 28 is not limited to metal and may alternatively be formed from rigid resin.

What is claimed is:

1. An injection needle assembly adapted to be used in cooperation with an endoscope having an insertion channel, comprising:

an elongate, flexible liquid feed tube adapted to be inserted in the insertion channel of the endoscope, and having a proximal end portion which is smaller in outer diameter than the other portions of the liquid feed tube;

a needle fixed to the distal end of the liquid feed tube and adapted to be stuck in the body wall;

a rigid connecting pipe which has an axial length substantially equal to that of the proximal end portion and is fitted around the outer peripheral surface of the proximal end portion of the liquid feed tube; and a substantially cylindrical connector having a fitting portion at one end opening thereof in which the connecting pipe is fixedly inserted and a connecting portion at the other end opening adapted to be connected to an injector for feeding a liquid into the liquid feed tube.

2. The injection needle assembly according to claim 1, wherein said liquid feed tube includes retaining means for holding the connecting pipe on the outer peripheral surface of the proximal end portion of the liquid feed tube.

3. The injection needle assembly according to claim 2, wherein said retaining means includes a shoulder portion formed on the boundary between the proximal end portion and the other portion of the liquid feed tube and abutting against one end of the connecting pipe, and the end edge of the proximal end portion bent radially outward to engage the other end of the connecting pipe.

4. The injection needle assembly according to claim 3, wherein the end edge of said proximal end portion is folded radially outward to be located on the outer peripheral surface of the connecting pipe.

5. The injection needle assembly according to claim 2, wherein said retaining means includes a projection formed on the outer peripheral surface of the liquid feed tube and abutting against one end of the connecting pipe and the end edge of the proximal end portion bent radially outward to engage the other end of the connecting pipe.

6. The injection needle assembly according to claim 1, wherein said connecting pipe is formed of metal.

7. The injection needle assembly according to claim 1, wherein said connecting pipe is formed of rigid resin.

8. The injection needle assembly according to claim 1, wherein said fitting. portion includes a fitting hole having a diameter substantially equal to the outside diameter of the connecting pipe, and said connecting pipe is fitted in the fitting hole by press fitting.

* * * * *